United States Patent

Nagano et al.

Patent Number: 4,560,686
Date of Patent: Dec. 24, 1985

[54] METHOD FOR TREATING CIRCULATORY DISEASES BY USING (2-LOWER ALKOXYPHENYL)PIPERAZINE DERIVATIVES

[75] Inventors: Hiroyuki Nagano; Mitiro Takagi; Noboru Kubodera, all of Saitama; Isao Matsunaga; Hiroyuki Nabata, both of Tokyo; Yasuhiro Ohba, Kanagawa; Kazushige Sakai, Tokyo; Shun-ichi Hata, Kanagawa; Yasumi Uchida, Chiba, all of Japan

[73] Assignee: Chugai Seiyaku Kabushiki Kaisha, Tokyo, Japan

[21] Appl. No.: 532,271

[22] Filed: Sep. 14, 1983

[30] Foreign Application Priority Data

Sep. 24, 1982 [JP] Japan .................. 57-165049

[51] Int. Cl.$^4$ .................. A61K 31/495; C07D 241/04
[52] U.S. Cl. .................. 514/255; 544/392; 544/393
[58] Field of Search .............. 544/392, 393; 424/250; 514/255

[56] References Cited

FOREIGN PATENT DOCUMENTS 683208 3/1964 Canada .................. 544/393
0304 4/1910 France .

OTHER PUBLICATIONS

De Antoni, Chem. Abst., vol. 74 (1971).
De Antoni et al., Chem. Abstracts, vol. 78:58460b.
Nagano et al., Chem. Abstract, vol. 100:6547p.

Primary Examiner—Donald G. Daus
Assistant Examiner—Cecilia Shen
Attorney, Agent, or Firm—Browdy and Neimark

[57] ABSTRACT

Compounds of the formula

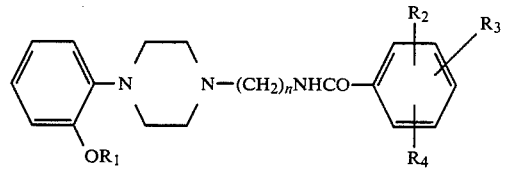

(wherein $R_1$ is a lower alkyl group, $R_2$, $R_3$ and $R_4$, which may be the same or different, represent a hydrogen atom, a halogen atom, a lower alkyl group, a lower alkoxy group, a hydroxyl group, a trifluoromethyl group or a lower alkoxycarbonyl group; two adjacent groups of $R_2$, $R_3$ and $R_4$ may combine to form a methylenedioxy group; n is an integer of 2 to 6) or salts thereof, are disclosed.

These compounds are useful as agents for treating circulatory diseases because they have hypotensive action and are capable of increasing the cerebral blood flow, decreasing the heart rate and suppressing ventricular arrhythmia due to myocardial ischemia.

3 Claims, No Drawings

METHOD FOR TREATING CIRCULATORY DISEASES BY USING (2-LOWER ALKOXYPHENYL)PIPERAZINE DERIVATIVES

The present invention relates to phenylpiperazine derivatives of formula (I) and salts thereof:

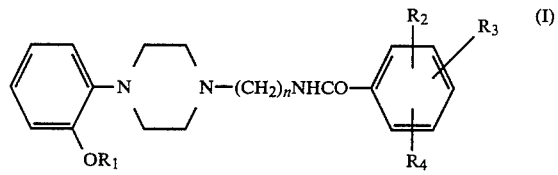

(I)

wherein $R_1$ is a lower alkyl group, preferably $C_1$–$C_3$ alkyl; $R_2$, $R_3$ and $R_4$, which may be the same or different, represent a hydrogen atom, a halogen atom, a lower alkyl group, preferably $C_1$–$C_3$ alkyl, a lower alkoxy group, preferably $C_1$–$C_3$ alkoxy, a hydroxyl group, a trifluoromethyl group, a lower alkoxycarbonyl group, preferably having $C_1$–$C_3$ alkoxy; two adjacent groups of $R_2$, $R_3$ and $R_4$ may combine to form a methylenedioxy group; n is an integer of 2 to 6.

The phenylpiperazine derivatives of formula (I) are novel compounds and can be produced by either of the following two methods:

(a)

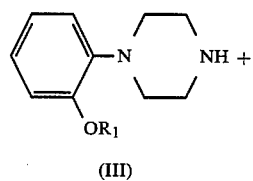

(III)

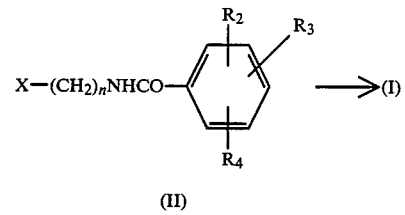

(II)

(b)

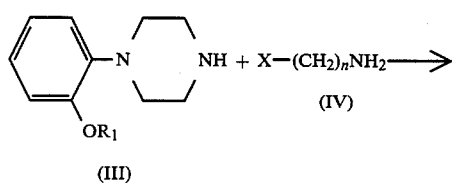

(III)    (IV)

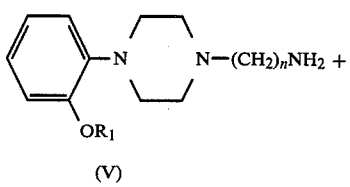

(V)

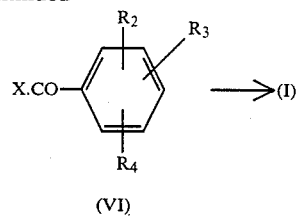

(VI)

wherein X is a halogen atom; $R_1$, $R_2$, $R_3$ and $R_4$ and n are the same as defined above.

The reaction represented by scheme (a) is performed by heating the reaction mixture in an inert solvent (e.g. benzene or toluene) under stirring for a few hours in the presence of a basic catalyst (e.g. sodium carbonate, potassium carbonate or triethylamine). The production of compound (V) from compounds (III) and (IV) is accomplished under the same conditions as used for reaction (a), and the resulting compound (V) can be subjected to the next stage of reaction without need for isolation. Reaction between compound (V) and an acid halide compound (VI) can be effected by a known method using an inert solvent in the presence of a base such as sodium carbonate. The reaction is preferably carried out at low temperatures. If the end compound (I) to be produced by reaction (a) or (b) has a hydroxyl group as at least one of $R_2$ to $R_4$, the hydroxyl group is preferably protected by an acyl group such as acetyl or benzoyl. Almost all protective groups are eliminated in the course of the reaction, and if not, the remaining protective groups can be readily removed by a conventional technique, such as hydrolysis.

In the reactions described above, the end compound (I) can be isolated from the reaction mixture by any conventional technique such as the addition of water to the reaction mixture, followed by separation of the organic layer, washing, drying concentration under vacuum, and recrystallization or column chromatography.

The compounds (I) of the present invention may form salts with organic or inorganic acids. Pharmaceutically acceptable acids are preferred, and inorganic examples are hydrochloric acid, sulfuric acid, nitric acid and phosphoric acid, and organic examples include fumaric acid, maleic acid, tartaric acid and succinic acid. Salts of the compounds (I) with these acids can be easily formed by any of the conventional methods.

The compounds of the present invention thus prepared are useful as agents for circulatory diseases because they cause decreases in systemic blood pressure and heart rate, and increase in cerebral blood flow, and in addition suppress ventricular arrhythmia relating to myocardial ischemia. These effects were examined in the following experiment.

To determine the useful effects of the compounds of the present invention, experiments were carried out on beagles. The animals were anesthetized by intravenous injection of pentobarbital sodium and were subjected to thoracotomy under artificial ventilation. In the experiments, the compounds of the invention were administered intravenously in the form of solutions of their bulk powders in distilled water. The following parameters were measured.

(1) Systemic blood pressure (SBP)

This parameter was measured with a pressure transducer by inserting a catheter into the right femoral artery. The results are shown in Table 1, wherein the symbol "↓" represents a pressure drop of about 10 mmHg and "↓ ↓" indicates a drop of about 20 mmHg. The identification number of the compounds shown in Table 1 correspond to that of the Examples described later in the specification (the same applies to Tables 2 and 3).

TABLE 1

| Compound No. | Dose (μg/kg) | SBP |
|---|---|---|
| 1 (b) | 1 | ↓ ↓ |
| 3 | 5 | ↓ |
| 5 | 5 | ↓ |
| 7 | 1 | ↓ ↓ |
| 10 | 1 | ↓ ↓ |
| 19 | 1 | ↓ |
| 21 | 1 | ↓ ↓ |
| 22 | 1 | ↓ ↓ |
| 30 | 1 | ↓ |
| 45 | 1 | ↓ |
| 51 | 1 | ↓ ↓ |

(2) Heart rate (HR)

This parameter was determined from the blood pulse with a cardiometer. The results are shown in Table 2 wherein the symbol "↓" indicates a decrease of 2.5–5% and "↓ ↓" refers to a greater decrease.

TABLE 2

| Compound No. | Dose (μg/kg) | HR |
|---|---|---|
| 1 (b) | 1 | ↓ ↓ |
| 7 | 1 | ↓ ↓ |
| 8 | 1 | ↓ ↓ |
| 10 | 1 | ↓ |
| 19 | 1 | ↓ |
| 20 | 1 | ↓ |
| 47 | 1 | ↓ |

(3) Total carotid artery blood flow (CaBF)

This parameter was determined with an electromagnetic flowmeter probe attached to the carotid artery. The results are shown in Table 3 wherein the symbol "↑" indicates a blood flow increase of about 10%, "↑ ↑" refers to an increase of about 50%, and "↑ ↑ ↑" shows a greater increase.

TABLE 3

| Compound No. | Dose (μg/kg) | CaBF |
|---|---|---|
| 7 | 1 | ↑ |
| 16 | 1 | ↑ |
| 18 | 1 | ↑ |
| 22 | 1 | ↑ ↑ |
| 43 | 1 | ↑ |
| 45 | 1 | ↑ ↑ ↑ |
| 51 | 1 | ↑ ↑ |

The agent for treating circulatory diseases which contains the compound of (I) according to the present invention may be administered to humans either orally or parenterally (i.e. intramuscularly, subcutaneously, intravenously or rectally). The compound may be formulated by a conventional technique into a suitable pharmaceutical composition in the form of tablets, granules, slow-release drugs, powders, capsules, suspensions, injections and suppositories. For the preparation of tablets, granules and powders, the compound (I) may be mixed with one or more pharmaceutical carriers such as excipients, binders or solvents (e.g. lactose, starch, mannitol, kaolin, crystalline cellulose, talc, calcium carbonate, and magnesium stearate). Capsules may be prepared by filling hard capsule casings with the granules or powder of the compound, and by filling soft capsule casings with solution of the compound in oil. The compound may also be suspended in an arabic gum or sucrose aqueous solution and the pH adjusted. The compound may be blended with mannitol to make it suitable for parenteral injection.

The compound (I) of the present invention should be incorporated in one of these pharmaceutical forms in amounts sufficient to exhibit the desired actions of treating or preventing circulatory diseases but not large enough to cause undesired side effects. A unit dosage form such as a tablet or capsule for oral administration usually contains about 0.05 to 30 mg of the active compound. For parenteral administration, a unit dosage such as a vial usually contains about 0.1 to 10 mg of the active compound. The daily dosage for adults varies from about 0.05 to 1,000 mg per adult, and the range of about 0.5 to 30 mg is preferred.

The present invention is described by the following examples which are given here for illustrative purposes only and are by no means intended to limit the scope of the invention.

EXAMPLE 1

(a) To 1.92 g (0.01 mol) of 1-(2-methoxyphenyl)piperazine, 1.01 g (0.01 mol) of triethylamine, 150 ml of toluene and 2.28 g (0.01 mol) of N-(2-bromoethyl)benzamide were added, and the mixture was refluxed for 3–4 hours under stirring. After the reaction, the solvent was concentrated under vacuum to half of its original volume, and a mixture of the residue with water was extracted with ethyl acetate. After separating the solvent layer, the aqueous layer was further extracted with ethyl acetate, and a mixture of the extract with the previously separated solvent layer was washed with water. To the organic layer, 1N HCl was added until the pH became 3.0, and the aqueous layer was separated. The separated aqueous layer was neutralized with aqueous sodium bicarbonate, and extracted with ethyl acetate. The organic layer was washed with water and a saturated aqueous solution of sodium chloride, dried with Glauber's salt, and distilled under vacuum to remove the solvent. The resulting residue was mixed with benzene-ether to provide 2.03 g (yield: 60%) of crystalline 1-(2-methoxyphenyl)-4-(2-benzoylaminoethyl)piperazine. Recrystallization from a mixture of isopropyl alcohol and ether gave a colorless needles having a melting point of 139°–140° C.

Elemental analysis Calculated for $C_{20}H_{25}N_3O_2$: C 70.77; H 7.42; N 12.38 (%); Found: C 70.92; H 7.47; N 12.41 (%).

(b) The crystalline 1-(2-methoxyphenyl)-4-(2-benzoylaminoethyl)piperazine prepared in (a) was dissolved in methanol and saturated with hydrogen chloride gas. The solution was concentrated to give a crystal of the piperazine in the hydrochloride form. Recrystallization from isopropanel gave a crystal having a melting point of 205°–206° C.

Elemental analysis Calculated for $C_{20}H_{25}N_3O_2 \cdot 2HCl$: C 58.25; H 6.60; N 10.19 (%). Found: C 58.47; H 6.61; N 10.15 (%).

EXAMPLES 2 TO 21

The compounds shown in Table 4 were prepared by repeating the procedure of Example 1.

became 3.0. The aqueous layer was separated, neutralized with sodium hydroxide and extracted with ethyl acetate. The resulting organic layer was washed with water, dried with Glauber's salt and concentrated under

TABLE 4

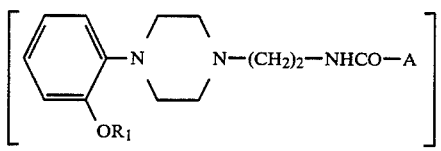

| Ex. No. | Substituent R₁ | A | Molecular formula | m.p. (°C.) | Calculated (%) C | H | N | Found (%) C | H | N |
|---|---|---|---|---|---|---|---|---|---|---|
| 2 | CH₃ | 2-chlorophenyl | $C_{20}H_{24}ClN_3O_2$ | 131–132 | 64.25 | 6.47 | 11.24 | 64.24 | 6.52 | 11.26 |
| 3 | CH₃ | 2-chlorophenyl | $C_{20}H_{24}ClN_3O_2 \cdot 2HCl$ | 212–213 | 53.76 | 5.87 | 9.40 | 53.89 | 5.92 | 9.34 |
| 4 | CH₃ | 3-chlorophenyl | $C_{20}H_{24}ClN_3O_2$ | 138–139 | 64.25 | 6.47 | 11.24 | 64.41 | 6.52 | 11.24 |
| 5 | CH₃ | 4-chlorophenyl | $C_{20}H_{24}ClN_3O_2$ | 162–163 | 64.25 | 6.47 | 11.24 | 64.36 | 6.52 | 11.37 |
| 6 | CH₃ | 2-fluorophenyl | $C_{20}H_{24}FN_3O_2$ | 90 | 67.21 | 6.77 | 11.76 | 67.32 | 6.81 | 11.74 |
| 7 | CH₃ | 2-fluorophenyl | $C_{20}H_{24}FN_3O_2 \cdot 2HCl$ | 197.5 | 55.82 | 6.09 | 9.76 | 55.79 | 6.04 | 9.68 |
| 8 | CH₃ | 3-fluorophenyl | $C_{20}H_{24}FN_3O_2$ | 132–133 | 67.21 | 6.77 | 11.76 | 67.26 | 6.78 | 11.71 |
| 9 | CH₃ | 4-fluorophenyl | $C_{20}H_{24}FN_3O_2$ | 135–136 | 67.21 | 6.77 | 11.76 | 67.36 | 6.79 | 11.71 |
| 10 | CH₃ | 4-fluorophenyl | $C_{20}H_{24}FN_3O_2 \cdot HCl$ | 244–245 | 60.99 | 6.40 | 10.67 | 61.15 | 6.43 | 10.68 |
| 11 | CH₃ | 2-bromophenyl | $C_{20}H_{24}BrN_3O_2$ | 146–147 | 57.42 | 5.78 | 10.04 | 57.54 | 5.82 | 10.02 |
| 12 | CH₃ | 2-methylphenyl | $C_{21}H_{27}N_3O_2$ | 132–133 | 71.36 | 7.70 | 11.89 | 71.55 | 7.78 | 11.95 |
| 13 | CH₃ | 2-trifluoromethylphenyl | $C_{21}H_{24}F_3N_3O_2 \cdot 2HCl$ | 180.5–181.5 | 52.61 | 5.47 | 8.77 | 52.34 | 5.43 | 8.59 |
| 14 | CH₃ | 3-methylphenyl | $C_{21}H_{27}N_3O_2$ | 128 | 71.36 | 7.70 | 11.89 | 71.41 | 7.72 | 11.87 |
| 15 | CH₃ | 4-methylphenyl | $C_{21}H_{27}N_3O_2$ | 132–133 | 71.36 | 7.70 | 11.89 | 71.40 | 7.71 | 11.88 |
| 16 | CH₃ | 2,6-dichlorophenyl | $C_{20}H_{23}Cl_2N_3O_2 \cdot HCl \cdot H_2O$ | 135–138 | 51.90 | 5.44 | 9.08 | 51.97 | 5.65 | 9.07 |
| 17 | CH₃ | 2,4-dichlorophenyl | $C_{20}H_{23}Cl_2N_3O_2$ | 139–140 | 58.83 | 5.68 | 10.29 | 59.00 | 5.71 | 10.35 |
| 18 | CH₃ | 2,6-difluorophenyl | $C_{20}H_{23}F_2N_3O_2 \cdot 2HCl$ | 224–224.5 | 53.59 | 5.62 | 9.37 | 53.38 | 5.61 | 9.20 |
| 19 | CH(CH₃)₂ | 2-fluorophenyl | $C_{22}H_{28}FN_3O_2 \cdot 2HCl$ | 188 | 57.64 | 6.60 | 9.17 | 57.62 | 6.61 | 9.16 |
| 20 | CH₂CH₂CH₃ | 2-fluorophenyl | $C_{22}H_{28}FN_3O_2 \cdot 2HCl$ | 208–210 | 57.64 | 6.60 | 9.17 | 57.61 | 6.59 | 9.21 |
| 21 | CH₂CH₃ | 2-fluorophenyl | $C_{21}H_{26}FN_3O_2 \cdot 2HCl$ | 206–207 | 56.76 | 6.35 | 9.46 | 56.72 | 6.34 | 9.38 |

EXAMPLE 22

To 1.92 g (0.01 mol) of 1-(2-methoxyphenyl)piperazine, 2,05 g (0.01 mol) of 2-aminoethylbromide hydrobromide, 2.5 g of triethylamine and 20 ml of n-butanol were added, and the mixture was refluxed for 6 hours. After the reaction, the mixture was concentrated under vacuum, and to the resulting residue, 2.5 g of anhydrous sodium carbonate, 20 ml of water and 20 ml of ethyl acetate were added. Under agitation with cooling on ice, a solution of 2.2 g (0.011 mol) of 2,3-dimethoxybenzoyl chloride in a small amount of ethyl acetate was added dropwise to the mixture. Thereafter, the mixture was stirred for 30 minutes under cooling with ice and extracted with ethyl acetate by agitation for 30 minutes at room temperature. The separated organic layer was washed with water, and 1N HCl was added until the pH became 3.0. The aqueous layer was separated, neutralized with sodium hydroxide and extracted with ethyl acetate. The resulting organic layer was washed with water, dried with Glauber's salt and concentrated under vacuum. The residue was subjected to column chromatography on silica gel (solvent: chloroform/methanol=100:1) to provide 1.99 g (yield: 50%) of 1-(2-methoxyphenyl)-4[2-(2,3-dimethoxybenzoyl)aminoethyl]piperazine. Recrystallization from isopropanol gave a colorless acicular crystal having a melting point of 133°–134° C.

Elemental analysis Calculated for $C_{22}H_{29}N_3O_4$: C 66.14; H 7.32; N 10.52 (%). Found: C 66.05; H 7.33; N 10.45 (%).

EXAMPLES 23 TO 29

The compounds shown in Table 5 were prepared by repeating the procedure of Example 22. Those in hydrochloride form were obtained by the same treatment as used in Example 1-b).

TABLE 5

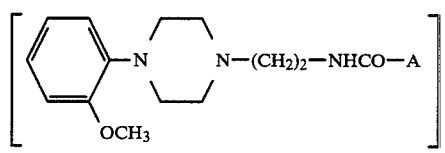

| Ex. No. | Substituent A | Molecular formula | m.p. (°C.) | Calculated (%) C | H | N | Found (%) C | H | N |
|---|---|---|---|---|---|---|---|---|---|
| 23 | 2-methoxyphenyl | $C_{21}H_{27}N_3O_3 \cdot HCl$ | 215–216 | 62.14 | 6.95 | 10.35 | 62.13 | 7.01 | 10.25 |
| 24 | 4-methoxyphenyl | $C_{21}H_{27}N_3O_3$ | 163–164 | 68.27 | 7.37 | 11.37 | 68.32 | 7.39 | 11.33 |
| 25 | 3,4,5-trimethoxyphenyl | $C_{23}H_{31}N_3O_5$ | 152 | 64.32 | 7.28 | 9.78 | 64.56 | 7.31 | 9.70 |
| 26 | 3,4-methylenedioxyphenyl | $C_{21}H_{25}N_3O_4$ | 129–130 | 65.78 | 6.57 | 10.96 | 65.91 | 6.55 | 10.92 |
| 27 | 3,4-dimethoxyphenyl | $C_{22}H_{29}N_3O_4$ | 149–150 | 66.15 | 7.32 | 10.52 | 66.14 | 7.31 | 10.64 |
| 28 | 2-ethoxyphenyl | $C_{22}H_{29}N_3O_3 \cdot 2HCl$ | 230–231 | 58.02 | 6.86 | 9.23 | 58.18 | 6.79 | 9.28 |

TABLE 5-continued

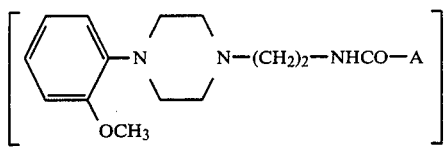

| Ex. No. | Substituent A | Molecular formula | m.p. (°C.) | Calculated (%) C | H | N | Found (%) C | H | N |
|---|---|---|---|---|---|---|---|---|---|
| 29 | 4-methoxycarbonylphenyl | $C_{22}H_{27}N_3O_4 \cdot 2HCl$ | 212 | 56.17 | 6.21 | 8.93 | 56.08 | 6.20 | 8.91 |

EXAMPLE 30

A mixture of 1.92 g (0.01 mol) of 1-(2-methoxyphenyl)-piperazine and 2.15 g (0.01 mol) of N-(3-chloropropyl)-4-fluorobenzamide was added to a mixture of toluene (20 ml) and triethylamine (2 ml) under agitation. The resulting mixture was gradually heated to the refluxing temperature at which the mixture was held for 5 hours. After completion of the reaction, the mixture was cooled and the precipitating salt was filtered off. The filtrate was extracted with 20 ml of benzene, and the extract was washed first with saturated aqueous sodium bicarbonate, then washed with water twice. By drying with anhydrous magnesium sulfate and subsequent concentration, 1-(2-methoxyphenyl)-4-[3-(4-fluorobenzoyl)aminopropyl]piperazine was produced as an oily substance. The oil was dissolved in methanol (30 ml) and the solution was saturated with hydrogen chloride gas. Upon concentration of the saturated solution, a crystal of the piperazine in hydrochloride form was obtained (2.9 g). m.p. 231.7° C. (recrystallized from ethanol).

Elemental analysis Calculated for $C_{21}H_{26}FN_3O_2 \cdot 2HCl$: C 56.76; H 6.35; N 9.46 (%). Found: C 56.71; H 6.38; N 9.50 (%).

EXAMPLES 31 TO 41

The compounds listed in Table 6 were prepared by repeating the procedure of Example 29.

EXAMPLE 42

(a) The oil of 1-(2-methoxyphenyl)-4-[3-(4-fluorobenzoyl)aminopropyl]piperazine produced in Example 30 was dissolved in methanol and the solution was treated with an equal volume of fumaric acid to give a crystal of the piperazine in fumarate form. m.p. 166° C. (recrystallized from ethanol-hexane).

Elemental analysis Calculated for $C_{21}H_{26}FN_3O_2 \cdot C_4H_4O_4$: C 61.59; H 6.20; N 8.62 (%). Found: C 61.62; H 6.23; N 8.61 (%).

(b) A maleate salt of 1-(2-methoxyphenyl)-4-[3-(4-fluorobenzoyl)aminopropyl]piperazine was prepared by repeating the procedure of (a) except that maleic acid was substituted for fumaric acid. m.p. 141° C.

Elemental analysis Calculated for $C_{21}H_{26}FN_3O_2 \cdot C_4H_4O_4$: C 61.59; H 6.20; N 8.62 (%). Found: C 61.60; H 6.25; N 8.59 (%).

EXAMPLE 43

A hydrochloride form of 1-(2-methoxyphenyl)-4-[5-(4-fluorobenzoyl)aminopentyl]piperazine was prepared by repeating the procedure of Example 29 except that N-(5-chloropentyl)-4-fluorobenzamide was substituted for N-(3-chloropropyl)-4-fluorobenzamide. m.p. 217° C. (recrystallized from ethanol).

Elemental analysis Calculated for $C_{23}H_{30}FN_3O_2 \cdot HCl$: C 63.37; H 7.17; N, 9.64 (%). Found: C 63.01; H 7.22; N 9.56 (%).

TABLE 6

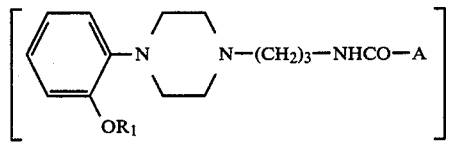

| Ex. No. | Substituent $R_1$ | A | Molecular formula | m.p. (°C.) | Calculated (%) C | H | N | Found (%) C | H | N |
|---|---|---|---|---|---|---|---|---|---|---|
| 31 | $CH_3$ | phenyl | $C_{21}H_{27}N_3O_2 \cdot 2HCl$ | 218–219 | 59.15 | 6.86 | 9.85 | 58.90 | 6.89 | 9.68 |
| 32 | $CH_3$ | 2-chlorophenyl | $C_{21}H_{26}ClN_3O_2 \cdot 2HCl$ | 205 | 54.73 | 6.12 | 9.12 | 54.70 | 6.16 | 9.14 |
| 33 | $CH_3$ | 3-chlorophenyl | $C_{21}H_{26}ClN_3O_2 \cdot 2HCl$ | 216 | 54.73 | 6.12 | 9.12 | 54.61 | 6.13 | 9.07 |
| 34 | $CH_3$ | 4-chlorophenyl | $C_{21}H_{26}ClN_3O_2 \cdot 2HCl$ | 236 | 54.73 | 6.12 | 9.12 | 54.78 | 6.13 | 9.06 |
| 35 | $CH_3$ | 2-fluorophenyl | $C_{21}H_{26}FN_3O_2 \cdot 2HCl$ | 204 | 56.76 | 6.35 | 9.46 | 56.60 | 6.35 | 9.33 |
| 36 | $CH_3$ | 2-methoxyphenyl | $C_{22}H_{29}N_3O_3 \cdot 2HCl$ | 199 | 57.89 | 6.85 | 9.21 | 57.76 | 6.98 | 8.97 |
| 37 | $CH_3$ | 2,3-dimethoxyphenyl | $C_{23}H_{31}N_3O_4 \cdot 2HCl$ | 172 | 56.79 | 6.84 | 8.64 | 56.73 | 6.81 | 8.74 |
| 38 | $CH_3$ | 2,4-dimethoxyphenyl | $C_{23}H_{31}N_3O_4 \cdot 2HCl$ | 185 | 56.79 | 6.84 | 8.64 | 56.72 | 6.79 | 8.69 |
| 39 | $CH_3$ | 3,4,5-trimethoxyphenyl | $C_{24}H_{33}N_3O_5 \cdot 2HCl$ | 162 | 55.81 | 6.83 | 8.14 | 55.91 | 6.75 | 8.07 |
| 40 | $CH_3$ | 2,3-methylenedioxyphenyl | $C_{22}H_{27}N_3O_4 \cdot 2HCl$ | 228 | 56.17 | 6.21 | 8.93 | 56.12 | 6.18 | 8.79 |
| 41 | $CH(CH_3)_2$ | 4-fluorophenyl | $C_{23}H_{30}FN_3O_2 \cdot 2HCl$ | 184 | 58.47 | 6.83 | 8.89 | 58.32 | 6.81 | 8.78 |

EXAMPLE 44

A hydrochloride form of 1-(2-methoxyphenyl)-4-[5-(2-methoxybenzoyl)aminopentyl]piperazine was prepared by repeating the procedure of Example 29 except that N-(5-chloropentyl)-2-methoxybenzamide was substituted for N-(3-chloropropyl)-4-fluorobenzamide. m.p. 184° C. (recrystallized from ethanol-water).

Elemental analysis Calculated for $C_{24}H_{33}N_3O_3 \cdot 2HCl \cdot \frac{1}{2}H_2O$: C 58.41; H 7.35; N 8.51 (%). Found: C 58.10; H 7.11; N 8.38 (%).

EXAMPLE 45

(a) To 1.92 g (0.01 mol) of 1-(2-methoxyphenyl)piperazine, 2.05 g (0.01 mol) of 2-aminoethyl bromide hydrobromide, 2.76 g (0.02 mol) of anhydrous potassium carbonate and 40 ml of n-butanol were added, and the mixture was refluxed for 6 hours. After the reaction, the mixture was concentrated under vacuum, and to the resulting residue, 2.5 g of anhydrous sodium carbonate, 20 ml of water and 20 ml of ethyl acetate were added. Under agitation with cooling on ice, 2.38 g (0.012 mol) of acetylsalicylic acid chloride as dissolved in a small amount of ethyl acetate was added dropwise to the mixture. Thereafter, the mixture was stirred for 30 minutes under cooling with ice and extracted with ethyl acetate by agitation for 30 minutes at room temperature. The separated organic layer was washed with water, and 1N HCl was added until the pH became 3.0. The aqueous layer was separated, neutralized with sodium hydroxide and extracted with ethyl acetate. The resulting organic layer was washed with water, dried with Glauber's salt and concentrated under vacuum. The residue was subjected to column chromatography on silica gel (solvent: chloroform/methanol=100:1) to provide 1.78 g (yield: 50%) of 1-(2-methoxyphenyl)-4-[2-(2-hydroxybenzoyl)aminoethyl]piperazine as an oily substance.

Elementary analysis Calculated for $C_{20}H_{25}N_3O_3$: C 67.58; H 7.09; N 11.82 (%). Found: C 67.58; H 7.08; N 11.81 (%).

(b) The oil produced in (a) was dissolved in ethanol and the solution was saturated with hydrogen chloride gas. Upon concentration, a crystal of the piperazine in hydrochloride form was obtained. m.p. 200°–202° C. (recrystallized from methanol/isopropanol)

Elemental analysis Calculated for $C_{20}H_{25}N_3O_3 \cdot 2HCl$: C 56.08; H 6.35; N 9.81 (%). Found: C 56.33; H 6.45; N 9.54 (%).

EXAMPLES 46 TO 51

The compounds listed in Table 7 were prepared by repeating the procedure of Example 45.

TABLE 7

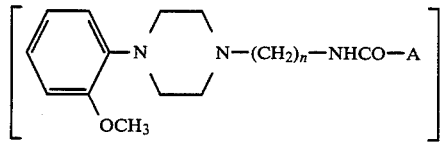

| Ex. No. | Substituent A | n | Molecular formula | m.p. (°C.) | Calculated (%) C | H | N | Found (%) C | H | N |
|---|---|---|---|---|---|---|---|---|---|---|
| 46 | 4-hydroxyphenyl | 2 | $C_{20}H_{25}N_3O_3 \cdot HCl$ | 255–256 | 61.30 | 6.69 | 10.72 | 61.58 | 6.77 | 10.65 |
| 47 | (2-hydroxy-5-chloro)-phenyl | " | $C_{20}H_{24}ClN_3O_3 \cdot 2HCl$ | 220–221 | 51.91 | 5.66 | 9.08 | 51.61 | 5.60 | 9.07 |
| 48 | 2,5-dihydroxyphenyl | " | $C_{20}H_{25}N_3O_4$ | 214 | 64.67 | 6.78 | 11.31 | 64.61 | 6.72 | 11.30 |
| 49 | 2,6-dihydroxyphenyl | " | $C_{20}H_{25}N_3O_4 \cdot 2HCl$ | 225–226.5 | 54.06 | 6.13 | 9.46 | 54.01 | 6.10 | 9.42 |
| 50 | 2-hydroxyphenyl | 3 | $C_{21}H_{27}N_3O_3 \cdot 2HCl$ | 221 | 57.01 | 6.61 | 9.50 | 56.98 | 6.59 | 9.47 |
| 51 | 2,5-dihydroxyphenyl | " | $C_{21}H_{27}N_3O_4 \cdot 2HCl$ | 213 | 55.03 | 6.38 | 9.17 | 55.21 | 6.46 | 9.07 |

We claim:

1. A method for treating arrhythmia or a disease treatable by an agent for vasodilating blood vessels which comprises administering to a patient in need of said treatment an effective amount for said treatment of a phenylpiperazine compound of the formula

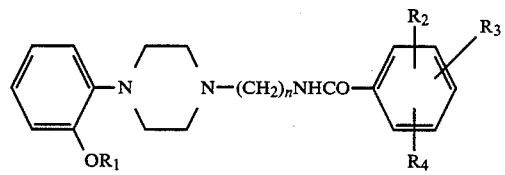

(wherein $R_1$ is $C_1$–$C_3$ alkyl group; $R_2$, $R_3$ and $R_4$, which may be the same or different, represent a hydrogen atom, a halogen atom, a $C_1$–$C_3$ alkyl group, a hydroxy group, a trifluoromethyl group or an alkoxycarbonyl group having a $C_1$–$C_3$ alkoxy group; n is an integer of 2 to 6) or a salt thereof.

2. A method in accordance with claim 1 wherein said phenylpiperazine is administered in an effective dosage of 0.5 to 30 mg per day.

3. A composition for treating arrhythmia or a disease treatable by an agent for vasodilating blood vessels which comprises a pharmaceutically effective carrier and an amount suitable for said treatment of a phenylpiperazine compound of the formula:

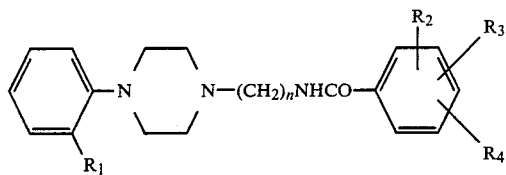

(wherein $R_1$ is a $C_1$–$C_3$ alkyl group; $R_2$, $R_3$ and $R_4$, which may be the same or different, represent a hydrogen atom, a halogen atom, a $C_1$–$C_3$ alkyl group, a hydroxy group, a trifluoromethyl group or an alkoxycarbonyl group having a $C_1$–$C_3$ alkoxy group; n is an integer of 2 to 6) or a salt thereof.

* * * * *

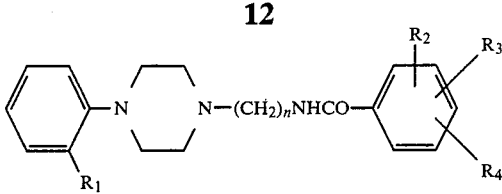

(wherein $R_1$ is a $C_1$–$C_3$ alkyl group; $R_2$, $R_3$ and $R_4$, which may be the same or different, represent a hydrogen atom, a halogen atom, a $C_1$–$C_3$ alkyl group, a hydroxy group, a trifluoromethyl group or an alkoxycarbonyl group having a $C_1$–$C_3$ alkoxy group; n is an integer of 2 to 6) or a salt thereof.

* * * * *